United States Patent [19]
Ranalletta

[11] Patent Number: 5,630,419
[45] Date of Patent: May 20, 1997

[54] SEALING CONNECTOR FOR MULTICONDUCTOR CABLES

[75] Inventor: Joseph V. Ranalletta, Englewood, Colo.

[73] Assignee: Tetrad Corporation, Englewood, Colo.

[21] Appl. No.: 359,465

[22] Filed: Dec. 20, 1994

[51] Int. Cl.$^6$ ............................................. A61B 8/00
[52] U.S. Cl. .............................. 128/662.03; 439/142
[58] Field of Search .................... 128/660.1, 661.01, 128/662.03; 439/135, 142, 271, 277, 213, 497; 174/52.1, 135, 73.1

[56] References Cited

U.S. PATENT DOCUMENTS

| | | | |
|---|---|---|---|
| 1,861,768 | 6/1932 | Wappler . | |
| 2,546,385 | 3/1951 | Christina . | |
| 2,786,245 | 3/1957 | Steinbock, Jr. . | |
| 2,806,123 | 9/1957 | Steinbock, Jr. . | |
| 2,962,688 | 11/1960 | Werner | 439/271 |
| 3,633,150 | 1/1972 | Swartz | 439/142 |
| 3,800,064 | 3/1974 | Lusk | 174/73.1 |
| 3,835,440 | 9/1974 | Clarke | 439/213 |
| 4,031,312 | 6/1977 | Coleman et al. | 174/52.1 |
| 4,059,322 | 11/1977 | Fellner | 439/142 |
| 4,537,458 | 8/1985 | Worth | 439/497 |
| 4,707,047 | 11/1987 | Michaels et al. | 439/271 |
| 5,070,881 | 12/1991 | Weiland | 128/662.03 |
| 5,120,512 | 6/1992 | Masuda . | |
| 5,137,689 | 8/1992 | Cantrell . | |
| 5,207,225 | 5/1993 | Oaks et al. | 128/661.01 |
| 5,225,160 | 7/1993 | Sanford et al. . | |

Primary Examiner—George Manuel
Attorney, Agent, or Firm—Michael de Angeli

[57] ABSTRACT

A sealable connector assembly for terminating a multiconductor cable, such as used for connecting electronic surgical instruments to devices for providing drive signals and analyzing return signals, comprises a body terminating in a flange having a planar distal edge. A cap member placed over the flange includes a planar gasket sealing to the planar edge of the flange, and secured to the connector by a locking member.

21 Claims, 2 Drawing Sheets

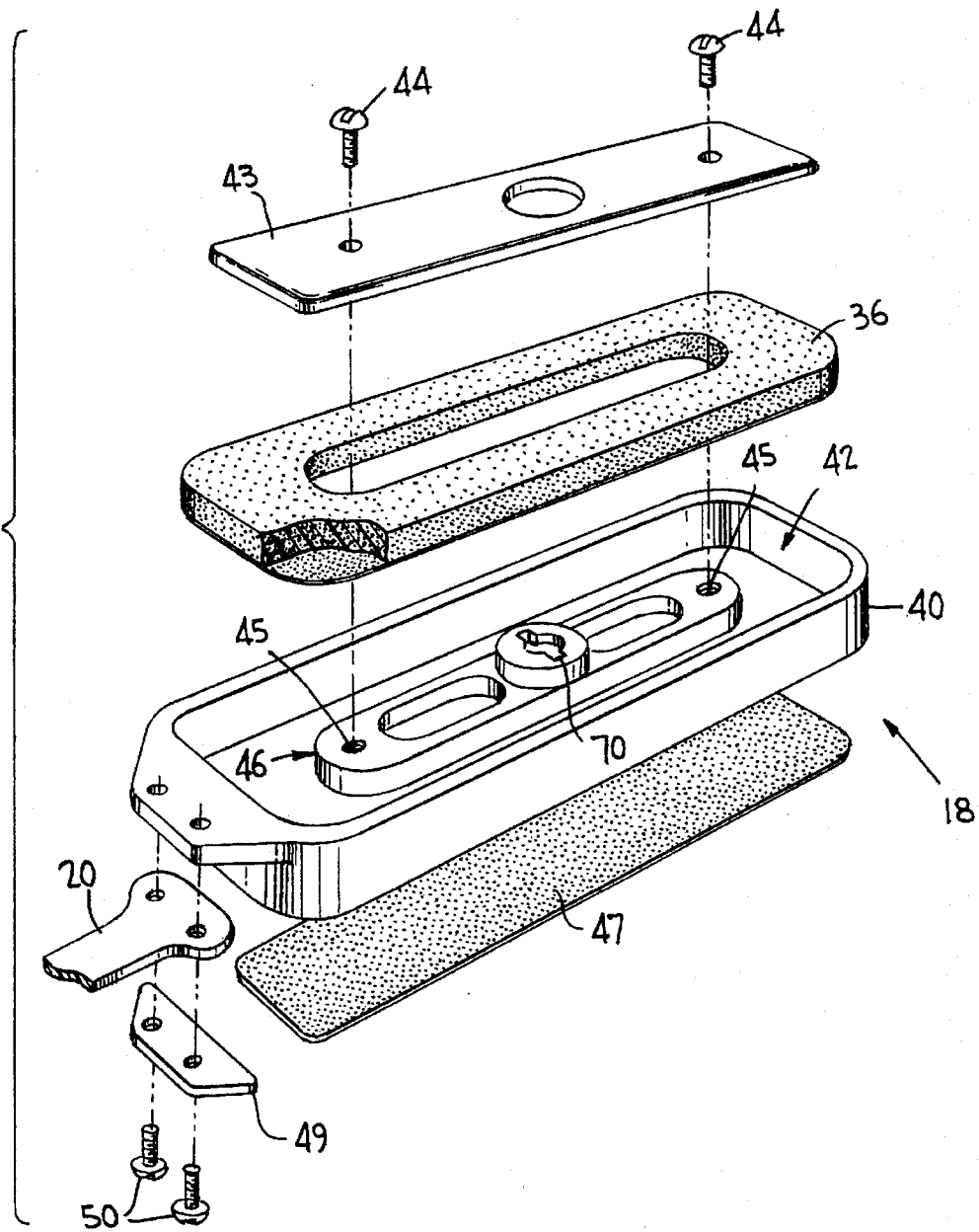

SEALING CONNECTOR FOR MULTICONDUCTOR CABLES

FIELD OF THE INVENTION

This invention relates to a sealing connector for multiconductor cables, useful for example in order to permit disinfection of electronic instruments comprising multi-pin connectors prior to surgical procedures, while avoiding exposure of the contact pins of the connector to the disinfecting medium.

BACKGROUND OF THE INVENTION

This invention relates to sealing connectors for multiconductor cables. Although the invention was made in the context of simplifying and rendering more reliable the disinfection of electronic equipment used in surgical procedures, the connector of the invention may have additional applications. As used herein, the terms "sterilization" and "disinfection" are essentially equivalent, although "sterilization" is generally understood to imply the destruction of all biological material on the items sterilized, while "disinfecting" means killing all pathogenic life forms, apart from certain bacteria in spore form. The methods and apparatus of the invention are useful for both.

Increasingly, surgical procedures are performed using probes inserted into the body of a patient, as such "least-invasive" procedures are safer, less traumatic, and less costly than traditional invasive "open" surgical techniques. Examples of such least invasive probes include endoscopic instruments for forming a visual image of a body joint, organ, or the like to be examined, as well as various types of probes for performing angioplasty and similar procedures, and ultrasonic probes for imaging body parts. Many such probes include a cable comprising a number of electric conductors for carrying signals to and from a probe head at the distal tip of the probe. This application specifically discusses ultrasonic probes, but it is to be understood that the invention claimed herein also relates to electronic probes as employed for other least-invasive and non-invasive surgical purposes, as well as to nonsurgical uses of the sealing connector of the invention.

In most circumstances, electronic probes used in surgical procedures are connected to external equipment by a multiple-conductor cable. In the example of an ultrasonic probe, such external equipment provides a drive signal to a transducer in a probe head to cause it to emit ultrasonic energy traveling into a body part to be examined. The external equipment similarly includes devices for processing return signals provided by the transducer responsive to detection of the ultrasonic energy after reflection within the body part to be imaged, and also includes various storage and display devices. To carry these drive and return signals, a number of conductors must be provided running along a multi-conductor cable between the external equipment and the transducer at the head of the probe. Accordingly, a complete probe assembly comprises a probe head, including the transducer, and a multi-conductor cable, terminated by a multi-pin connector, by which the probe assembly is connected to the external equipment. An intermediate cable may be provided between the multi-pin connector terminating the probe cable and the external equipment.

It is essential to either sterilize the probe or to prevent contact between an unsterilized probe and the patient. There are currently available no fully satisfactory methods of sterilizing certain delicate surgical instruments incorporating electronic equipment.

Normal surgical disinfection and sterilization processes would involve exposure of the entire probe assembly, comprising, as noted above, the probe head, the multiconductor cable and, preferably, the multi-pin connector terminating the cable, to a disinfecting medium, either fluid or gas. Disinfecting media at room temperature or at moderately elevated temperatures (e.g., 150° F.) are desirably employed for disinfection of electronic surgical equipment, as such equipment is vulnerable to high-temperature autoclaving or steam disinfection processes.

Disinfection of an electronic probe comprising a cable terminated by a multi-pin cable connector poses several difficulties. If the connector's contact pins are exposed to and wetted by disinfecting fluids, they may corrode, interfering with their proper connection. Accordingly, a common practice is to place a fluid-tight protective cap over a ferrule in the connector housing extending around the contact pins, so as to seal the contact pins from the disinfecting medium. However, prior art caps often leak, especially if the sealing element is an O-ring or the like subjected to friction when the cap is placed over a ferrule surrounding the aperture in the connector through which the contact pins protrude, as is commonly the case. Alternatively, the cable connector itself may be maintained outside the sterile field, so that the cable connector need not be disinfected. However, this requires a person outside the sterile field to connect the probe to the external equipment (or to an intermediate cable, if used) while a surgeon or other person within the sterile field is obliged to handle the sterilized probe end.

Another possibility is to encase the probe itself in a thin rubber or plastic sheath, thus preventing the patient from being touched by a nondisinfected probe. However, this solution is not satisfactory in connection with ultrasonic probes, wherein direct connection of the transducer to the tissue to be imaged is important. This solution is also useless in connection with probes providing aspiration or irrigation, requiring one or more lumens in communication with the probe head, nor where an optical image must be formed, as the sheath would interfere with optical transmission. Further, it appears likely that in the near future even devices that are sheathed in use will be required to be disinfected.

More specifically, disinfection is commonly accomplished by immersing the probe head and cable, using a "high-level" disinfectant such as that sold as "Cidex 7", in an open tray for ten to thirty minutes prior to use, while allowing the cable connector, with the contact elements exposed, to simply remain outside the tray. Sterilization is accomplished similarly, but involves a much longer period of exposure to the disinfectant, typically ten to 24 hours. Both involve the difficulties mentioned above, namely, that the connector can be damaged if accidentally exposed to the disinfectant, and that two persons are required to make the connection of the equipment to an external instrument, power supply or the like.

Alternatively, delicate electronic surgical equipment that cannot withstand high temperature sterilization can be sterilized by exposure to ethylene oxide (EtO). While this gas does not damage or corrode the electrical connectors used, its use has several inherent difficulties. First, EtO is toxic, such that government regulations restrict its use. EtO is also commonly mixed with freon, to reduce its explosiveness; freon is in the process of being banned. Further, EtO sterilization is very time-consuming.

More recently, there have been developed self-contained sterilization units (see U.S. Pat. No. 5,225,160 to Sanford et al) that are capable of sterilizing various sorts of equipment in a convenient and rapid fashion. In use of these units, the equipment to be sterilized is disposed in a sealable chamber, and the interior and exterior surfaces thereof are exposed to a liquid chemical sterilant, under controlled temperature and pressure conditions, followed by a controlled water rinsing step. However, this system cannot be used without exposing the entire device to be sterilized to the sterilant, and thus is not useful for sterilizing electronic instruments having unprotected connectors for connection to external devices. As noted, prior art caps shielding the connector pins from the sterilant are insufficiently reliable to solve this problem.

According to the invention of commonly-assigned Ser. No. 08/152,135, filed Nov. 16, 1993, the sterilizing equipment may be provided with a dummy connector, to which the cable connector is sealed during sterilization. However, this solution requires redesign of the sterilizer equipment, which may be too costly for some users.

Therefore, it is apparent that there exists a need for an efficient and convenient sealable connector assembly, e.g., for an electronic probe comprising a probe head connected by a multiple-conductor cable to a multi-pin connector for connection to external equipment, such that the entire probe assembly, including the connector, can be disinfected simultaneously, without exposing the contact pins of the multi-pin connector to the disinfecting medium.

The following patents relate generally to the subject of disinfection of surgical or dental equipment.

Wappler U.S. Pat. No. 1,861,768 shows a basic "fumigating" sterilizer unit, including a sealed chamber having internal gas outlets for connection to the interior of catheters and the like.

Steinbock U.S. Pat. No. 2,786,245 shows a sterilizer tray including hollow posts for holding dental handpieces upright for drainage after sterilization. The dental tray is perforated to allow it to be lowered into a sterilizing fluid or the like. A second Steinbock patent, U.S. Pat. No. 2,806,123, is generally similar.

U.S. Pat. No. 5,120,512 to Masuda recognizes the difficulty of sterilizing a precision instrument such as a dental handpiece using steam or ethylene oxide gas, and shows a ozonating chamber for bacteriostatic purposes. Various devices may be connected to mating fittings for sterilizing their interior passages.

U.S. Pat. No. 5,137,689 to Cantrell shows a sterilizing device wherein instruments are connected by pressure fittings to receive pressurized sterilizing fluid for cleaning their internal surfaces.

U.S. Pat. No. 2,546,385 to Christina shows a custom-fitted tray for efficient receiving and cleaning of ampules for medicines and the like.

As noted above, U.S. Pat. No. 5,225,160 to Sanford et al shows a system for decontaminating and sterilizing medical instruments such as endoscopes, wherein an antimicrobial liquid may be sprayed on the exterior surface of the instrument and be supplied to the internal surfaces thereof.

As indicated above, the disinfection of an electronic probe used in surgical procedures presents a special problem not solved by the prior art patents discussed above.

OBJECTS AND SUMMARY OF THE INVENTION

It is therefore an object of the invention to provide a sealable connector assembly for a multiconductor cable such that a probe assembly or the like comprising the connector assembly can be sterilized, without danger of contamination of the contact pins of the connector by a liquid sterilant.

It is a further object of the invention to provide such a sealable connector assembly capable of being connected to preexisting connections on associated external equipment, e.g., for providing drive signals and analyzing and displaying return signals, such that the associated external equipment does not require modifications.

These and other objects of the invention which will be apparent as the discussion below proceeds are satisfied by the present invention, wherein a main body of the connector comprises a flange surrounding connecting pins provided for connection to an associated connector, the flange forming a distal edge lying in a single plane. A cap assembly is provided including a planar foam gasket arranged to contact the distal edge of the flange when the cap is urged against the body of the connector. A control mechanism used to secure the connector to associated external equipment is also used to secure the cap to the connector. The control mechanism is sealed to the main body of the connector, as is the cable strain relief provided. In the preferred embodiment, the gasket is a closed-cell silicone foam member compressed upon actuation of the control mechanism, so that no additional springs or the like are required to retain the cap on the connector assembly in the sealed configuration.

BRIEF DESCRIPTION OF THE DRAWINGS

The invention will be better understood if reference is made to the accompanying drawings, in which:

FIG. 3 shows an exploded perspective view of the cap assembly provided according to the invention.

DESCRIPTION OF THE PREFERRED EMBODIMENTS

Figure 1:
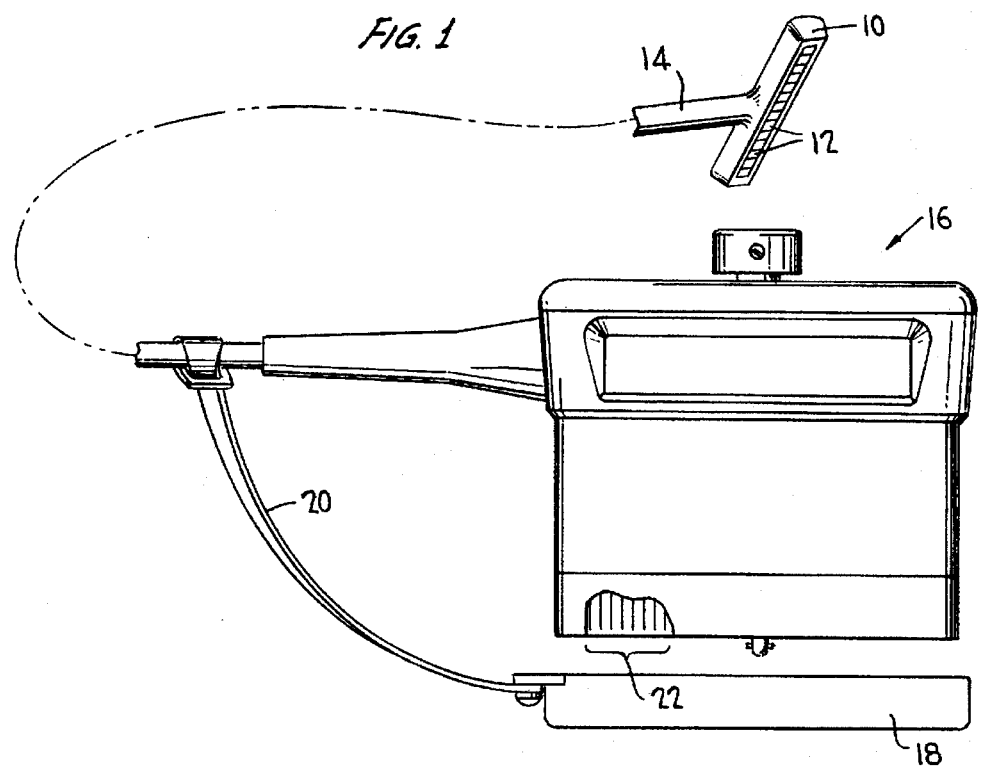
FIG. 1 shows a schematic view of the connector assembly according to the invention, and its connection to an ultrasonic probe, as an example of use of the connector assembly according to the invention.

As indicated above, it is a principal object of the invention to provide a sealable connector assembly for a multiconductor cable, for example, as used to connect an ultrasonic probe to associated external equipment providing drive signals for exciting the transducer of the probe and processing the return signals. FIG. 1 shows an ultrasonic probe assembly comprising, as is generally conventional, a probe head 10 including a number of piezoelectric transducer elements 12 and connected by a multiconductor cable 14 to the multiple-pin connector assembly 16, whereby the probe is effectively connected to the associated external equipment. As discussed above, before such a probe can be used on human subjects it must be sterilized by long term exposure to a sterilant liquid, typically at somewhat elevated temperature. In order that the probe assembly can be effectively sterilized, the connector 16 is provided according to the invention with a sealing cap assembly 18, which may desirably be retained on the cable 14 by a flexible strap 20. By provision of the sealing cap 18, the entire probe assembly shown in FIG. 1 can be disposed in the sterilant liquid for extended periods of time without danger of damage to the connector's contact pins 22, whereby the conductors of cable 14 are connected to associated external equipment for providing drive signals to the piezoelectric elements 12, and for analyzing reflected ultrasonic energy.

Figure 2:
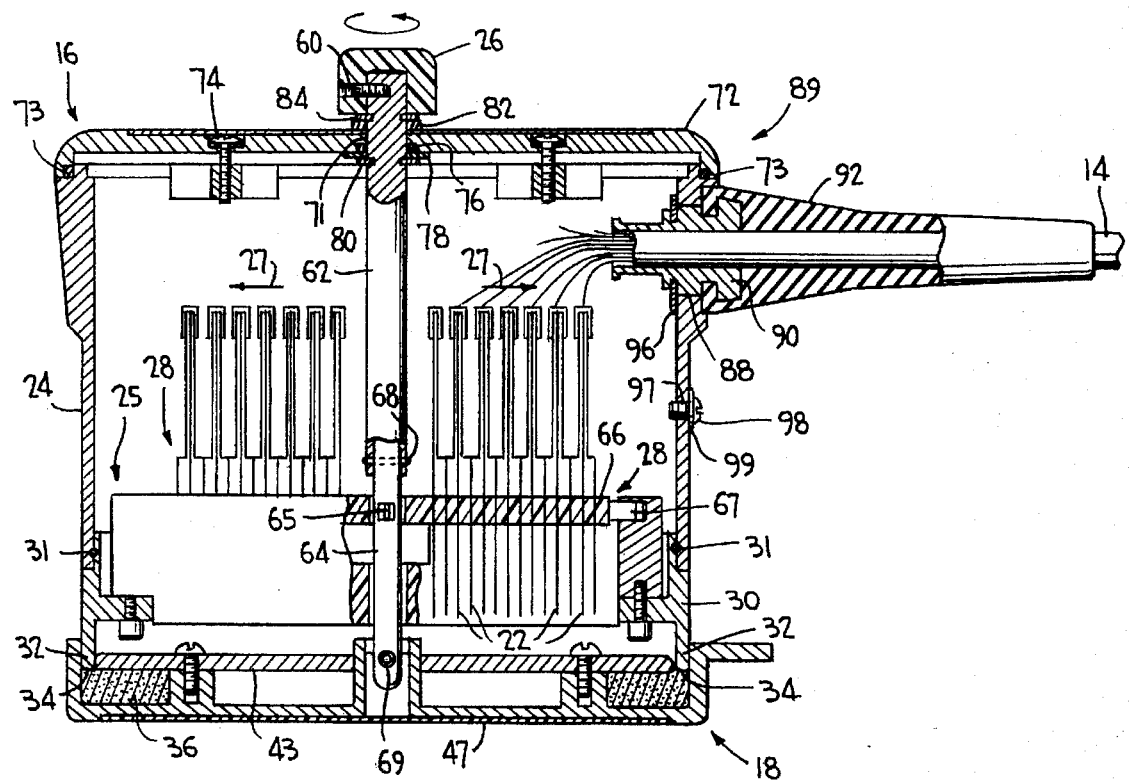
FIG. 2 shows a cross-sectional view through the main body of the connector and sealing cap assembly provided according to the invention, illustrating the position of the contact pins therein.

FIG. 2 shows a cross-sectional view of the body 24 of the connector 16 according to the invention, together with a cross-sectional view of the cap 18. In the embodiment shown, the connector body 24 is generally tubular, and rectangular in cross-section, to house a conventional "zero-insertion-force" connector mechanism 25, e.g., that sold as part number DL-156-PW6 by ITT Cannon of Santa Ana, Calif. The connector mechanism 25 includes opposed connector assemblies 28 moved laterally outwardly, as indicated by arrows 27, upon rotation of the control knob 26, such that pins 22 move laterally and engage mating contacts of an associated connector (not shown). See commonly assigned U.S. Pat. No. 5,368,496 for further general discussion of zero-insertion-force connectors. The precise design of the connector mechanism 25 is not material to the present invention; the improved sealing connector assembly of the invention is useful in sealing connectors other than zero-insertion-force connectors.

Returning more specifically now to the discussion of FIG. 2, the connector mechanism 25 is mounted in a bezel 30. The bezel 30 is mounted to body portion 24 of the connector and sealed thereto by O-ring 31, and is not detached therefrom under ordinary circumstances. Bezel 30 comprises an outer peripheral flange 32 having a distal sealing edge 34 which lies in a single plane generally parallel to the plane including connector pins 22, and which forms a seal with a resilient gasket 36 when cap assembly 18 is secured to connector 16.

FIG. 3 shows details of cap assembly 18, comprising a generally flat gasket 36 of resilient material contacted by the distal edge 34 of flange 32 (FIG. 2) to form a sealing connection between the cap assembly 18 and connector 16. Cap assembly 18 comprises a substantially rigid cover member 40 having a recess indicated at 42 therein for receiving resilient gasket 36 of generally square-ended oval or "racetrack" configuration, as shown, for sealingly engaging edge 34 of flange 32. Gasket 36 is secured in recess 42 by a retainer 43 in turn secured to cover member 40 by a pair of screws 44 or like fasteners engaging threaded holes 45 in a raised center section 46 of cover member 40. A strap 20 may be secured to cover member 40 by a further pair of screws 50 prevented from damaging strap 20 by a plate 49; as indicated in FIG. 1, strap 20 may be secured around the multiconductor cable connecting the probe head with the connector 16, ensuring that cap assembly 18 is not lost when not in use.

In the preferred embodiment, the gasket 36 may be die-cut of a sheet of closed-cell silicone foam material 0.25 inches thick, such as that sold by Boyd Corporation of Denver, Colo. as Product R10460. This is available with a layer of waterproof adhesive on one side, protected by a release paper until needed. This simplifies the handling of the gasket 36; upon assembly of gasket 36 to the cover member 40, the release paper is simply removed and the gasket pressed firmly into place. The retaining plate 43 is then assembled over gasket 36 and secured to cover member 40 by screws 45. Retaining plate 43 may be formed of a hard plastic, aluminum, or like material. If the mechanism whereby the cap assembly 18 is secured to the body 24 of the connector is such that its convenient manufacture requires a through-hole in cap assembly 18, such as the keyhole-shaped aperture 70 provided in the preferred embodiment, as discussed below, the rear of the cap assembly 18 is sealed by an outer plate 47 adhesively bonded to the cover member 40.

It is conventional in the art to secure zero-insertion-force connectors to mating connectors by rotatable control elements having transverse pins therein, such that when the tip of the control element having the pin therein is inserted into a keyhole-shaped aperture in the mating connector and rotated, the connector is secured to the mating connector assembly. The same locking mechanism is employed in the preferred embodiment of the present invention, so that it can be used with preexisting mating connectors, but of course the invention is not limited thereby.

In the embodiment shown, the rotatable control knob 26 is secured by a set screw 60 to a control shaft 62. As noted, the contact pins 22 may be provided as part of a standard zero-insertion-force connector mechanism 25, including a further control rod 64 having cams 65 for moving connector assemblies 28 laterally outwardly against the bias of leaf springs 67 upon rotation of rod 64. Rod 62 is provided with a roll pin 68 fitting therethrough to provide a torque-transmitting connection to rod 64. Rod 64 has a further transverse pin 69 formed therein for being received within a keyhole-shaped aperture 70 formed in the cover member 40 of cap assembly 18 (see FIG. 3). Therefore, when cap assembly 18 is placed over a first aperture of the connector 24 surrounding pins 22, such that the tip of the control rod 64 having pin 69 therein enters the keyhole-shaped aperture 70, and rod 64 is rotated by way of control knob 26, the cap 18 is secured sealingly against the connector 24.

In this embodiment, the dimensions of the parts are such that the foam gasket 36 must be compressed somewhat by the distal edge 34 of the flange 32, e.g., by the user's hand pressure, in order that pin 69 can enter keyhole-shaped aperture 70, in the process of securing of the cap to the connector 24. The compression of the foam 36 provides sufficient friction between pin 69 and the rear side of the central section 46 of the cap member 40 surrounding keyhole-shaped aperture 70 so that no additional springs or the like are required to prevent accidental dislodgement of the cap 18 from the connector 16. However, it will be appreciated that other forms of control members and locking assemblies might be provided within the scope of the invention as defined by the attached claims. Specifically, in this embodiment, the control member 26, along with rods 62 and 64, are rotated to secure the cap assembly 18 to the connector 16; a control rod assembly might also be pulled axially through the connector 16 to secure the cap assembly 18 thereto. This and other modifications are within the scope of the invention.

In the embodiment shown, the cap-securing mechanism is such that control rod 62 passes through body 24, and is rotated to secure the cap 18 to the body 24. A seal must be provided where the control rod 62 passes through a second aperture 71 in communication with the internal volume of the body 24 of the connector. As shown, this second aperture 71 is conveniently formed in a separate closure member 72 secured to the tubular body portion 24 by further screws 74 and sealed thereto by a further O-ring 73. Control rod 62 is sealed to the second aperture 71 by an O-ring 76 retained in a groove in closure member 72 and urged thereagainst by a washer 78 retained with respect to shaft 62 by a circlip 80 fitting into a mating groove on shaft 62. A further washer 82 formed of a plastic material is provided between the outer surface of the closure member 72 and the control rod 62, and is secured in position by a second circlip 84 fitting into a second groove formed in control rod 62.

The multiconductor cable 14 is provided with a sealed entry into the interior volume of the body 24 of the connector 18 by way of a further aperture 88. A seal is provided between cable 14 and body 24 of the connector by a strain relief assembly 89, comprising a core member 90 of a non-resilient material, such as aluminum, and a resilient sealing member 92. The resilient member 92 may be molded over the core member 90 of a polyvinylchloride plastic or the like. Core member 90 desirably has a keyed cross-section mating with aperture 88 of like cross-section in the body 24, such that the strain relief assembly 89 cannot be twisted with respect to body 24, protecting the conductors 94 of the multiconductor cable 14. Satisfactory results have been obtained by making these mating cross-sections square with rounded corners for ease of assembly.

The resilient member 92 is sized such that when the strain relief assembly 89 comprising the resilient member 92 and the core member 90 is pulled firmly into engagement with the body 24, a good seal is formed therebetween. The strain relief assembly 89 is secured to the body 24 by a spring clip 96 fitting into a mating groove formed in core member 90.

In some circumstances, e.g., during sterilization with EtO gas, the probe assembly may be placed in an evacuated chamber for sterilization. If a partial vacuum is formed within the internal volume of connector body 24 during this process, it may be very difficult to remove the cap assembly 18 if used. (As noted, EtO ordinarily will not affect the connector pins, so that the cap assembly may be omitted during EtO sterilization.) Accordingly, a pressure-equalizing screw 98 is provided, sealed to a further aperture 97 in body 24 by a washer 99; screw 98 can simply be eased to equalize pressure internal and external to the internal volume of body 24.

Thus, according to the invention, the body 24 of the connector 18 is provided with a first aperture, through which the contact pins 22 protrude, and which is sealed upon assembly of cap 18 thereto; a second aperture 71, through which the control element 62 extends, and which is sealed by O-ring 76 and washer 82; and a third aperture 89, through which the multiconductor cable 86 extends, and which is sealed by the strain relief assembly 89. The cap assembly 18 is secured to the body 24 by a hand-actuated control knob 26; in the embodiment shown, when knob 26 is rotated, pin 68 disposed behind keyhole-shaped aperture 70 in cover member 40 locks the cap to the body. The resilient nature of the gasket 36 provides sufficient frictional force to preclude accidental dislodgement of the cap 18 from the body 24. Other means of locking the cap to the body are within the scope of the invention. The body of the connector is generally tubular, being rectangular in cross-section in the embodiment shown; one open end of the tubular body is filled by the connector pin mechanism 22 and is sealed by the cap assembly 18, while the opposed end is sealed by a closure member 72 through which the control member 62 extends.

While a preferred embodiment of the invention has been described in detail, this should not be considered as a limitation on the invention, but merely as exemplary thereof. The invention is to be limited only by the claims which follow.

I claim:

1. A sealable connector assembly for terminating a multi-conductor cable, comprising:

a body, defining an internal volume, and defining a first aperture in communication with said internal volume, through which first aperture extend a plurality of connecting pins, for mating connection with a like plurality of pins on a mating device, said first plurality of connecting pins lying generally in a plane, and said aperture being surrounded by an upstanding flange, said flange having a continuous distal edge lying in a second plane parallel to the plane of said first plurality of connecting pins;

a cable strain relief sealed to said body at a second aperture extending through said body into said internal volume at a location spaced from said first aperture;

a multi-conductor cable extending through and sealed to said cable strain relief, and comprising a number of conductors connected to said first plurality of connecting pins;

a cap assembly adapted to be secured to said body to provide a seal around said distal edge of said flange, said cap assembly comprising:

a substantially rigid cover member defining a recess having a planar bottom surface of dimensions exceeding the dimensions of said flange in said second plane;

a resilient gasket fitting within said recess in said cover member, for sealingly engaging said distal edge of said flange; and means for retaining said gasket in said recess; and means for urging said cap assembly into sealing engagement with said body, without requiring relative rotation of said cap with respect to said body, such that said gasket is compressed against said distal edge of said flange, sealing said first plurality of pins and the internal volume of said body;

said means for urging said cap assembly into sealing engagement with said body comprising an elongated control element extending through said body, wherein a distal end of said control element is adapted to be secured to said cap assembly and a proximal end of said control element extends out of said body through a third aperture spaced from said first and second apertures, means for sealing said control element to said body at said third aperture, and hand-actuable means operatively connected to said proximal end of said control element for operating said control element to urge said cap assembly into sealing engagement with said body.

2. The connector assembly of claim 1, wherein said resilient gasket is a planar member cut from a sheet of material.

3. The connector assembly of claim 2, wherein the material of said gasket is a closed-cell silicone foam.

4. The connector assembly of claim 2, wherein said means for retaining said gasket in said recess comprises a substantially rigid planar member of dimensions fitting within said flange when said cap assembly is secured to said body and secured to said cover member, confining said gasket within said recess.

5. The connector assembly of claim 4, wherein said gasket is further adhesively retained in said recess.

6. The connector assembly of claim 1, wherein said first plurality of pins are arranged in generally rectangular configuration, such that said flange defines a rectangular opening, and wherein said gasket is of generally square-ended oval configuration.

7. The connector assembly of claim 1, wherein said control element is rotated by said hand-actuable means to secure said cap assembly in sealing relation to said body.

8. The connector assembly of claim 7, wherein said distal end of said control element comprises a transverse pin, received within a keyhole-shaped aperture in said cap assembly, and rotated to secure said cap assembly to said body.

9. The connector assembly of claim 7, wherein said means for sealing said control element to said body at said third aperture comprises an O-ring confined between said control element and said body.

10. The connector assembly of claim 9, wherein said means for sealing said control element to said body at said third aperture further comprises a seal member disposed around the end of said control member protruding from said body, and confined against said body.

11. The connector assembly of claim 1, wherein upon securing of said cap assembly to said body employing said means for securing, said resilient gasket is compressed sufficiently to exert a biasing force between said cap assembly and said body to preclude slipping of said means for securing said cap assembly to said body.

12. The connector assembly of claim 11, wherein said resilient gasket is formed of closed-cell silicone foam.

13. The connector assembly of claim 1, further comprising a pressure-equalizing means controllably sealing a further aperture connecting said internal volume with respect to the atmosphere.

14. The connector assembly of claim 13, wherein said pressure-equalizing means comprises a valve member in said further aperture for sealing said aperture.

15. In combination, the sealable connector assembly of claim 1, and an electronic surgical instrument comprising a probe head including at least one active element connected to said conductors of said multiconductor cable.

16. The combination of claim 15, wherein said instrument is an ultrasonic probe comprising a plurality of individual transducer elements connected to conductors of said cable.

17. A sealable connector assembly for terminating a multi-conductor cable, comprising:

a body, defining an internal volume, and defining a first aperture in communication with said internal volume, through which first aperture extend a plurality of connecting pins, for mating connection with a like plurality of pins on a mating device, said first plurality of connecting pins lying generally in a plane, and said aperture being surrounded by an upstanding flange, said flange having a continuous distal edge lying in a second plane parallel to the plane of said first plurality of connecting pins;

a cable strain relief sealed to said body at a second aperture extending through said body into said internal volume at a location spaced from said first aperture, said cable strain relief comprising a substantially non-resilient core member having a resilient member molded thereover, and means for urging said resilient member of said cable strain relief into sealing engagement with a peripheral edge of said second aperture in said body, such that said resilient member seals said strain relief to said body;

a multi-conductor cable extending through and sealed to said cable strain relief, and comprising a number of conductors connected to said first plurality of connecting pins;

a cap assembly adapted to be secured to said body to provide a seal around said distal edge of said flange, said cap assembly comprising:

a substantially rigid cover member defining a recess having a planar bottom surface of dimensions exceeding the dimensions of said flange in said second plane;

a resilient gasket fitting within said recess in said cover member, for sealingly engaging said distal edge of said flange; and <means for retaining said gasket in said recess; and means for urging said cap assembly into sealing engagement with said body, without requiring relative rotation of said cap with respect to said body, such that said gasket is compressed against said distal edge of said flange, sealing said first plurality of pins and the internal volume of said body.

18. The connector assembly of claim 17, wherein said means for urging said resilient member of said cable strain relief into sealing engagement with a peripheral edge of said second aperture in said body comprises a spring clip received in a circular groove in said core member, such that said spring clip urges a surface of said strain relief against a mating external surface of said body, forming an effective seal therebetween.

19. The connector assembly of claim 17, wherein said core member is keyed to said second aperture such that said strain relief is precluded from rotation with respect to said second aperture.

20. The connector assembly of claim 19, wherein said core member is keyed to said second aperture by being generally square in cross-section, said second aperture being similarly generally square.

21. A sealable connector assembly for terminating a multi-conductor cable, comprising:

a body, said body comprising a generally tubular housing, a plurality of connector pins disposed in said body and extending through a first aperture defined by a first open end of said tubular housing, an opposed open end of said housing being closed by a closure member sealed to said housing around mating peripheries thereof;

said connector pins being mounted for lateral movement within said body for contacting a like plurality of pins on a mating device, said first aperture being surrounded by an upstanding flange having a continuous distal edge;

a cable strain relief sealed to said body at a second aperture extending through said body into said internal volume at a location spaced from said first aperture;

a multi-conductor cable extending through and sealed to said cable strain relief, and comprising a number of conductors connected to said first plurality of connector pins;

a cap assembly adapted to be secured to said body to provide a seal around said distal edge of said flange, said cap assembly comprising:

a substantially rigid cover member defining a recess having a planar bottom surface of dimensions exceeding the dimensions of said flange in said second plane;

a resilient gasket fitting within said recess in said cover member, for sealingly engaging said distal edge of said flange; and means for retaining said gasket in said recess; and means for urging said cap assembly into sealing engagement with said body, such that said gasket is compressed against said distal edge of said flange, sealing said first plurality of pins and the internal volume of said body;

said means for urging said cap assembly into sealing engagement with said body such that said gasket is compressed against said distal edge of said flange comprising a control assembly, said control assembly comprising an elongated control element extending through said body and hand-actuable means for operating said control element, said control element comprising means on a distal end thereof for being secured to said cap assembly and means for moving said connector pins laterally to contact corresponding pins of a mating connector, said hand-actuable means being operatively connected to a proximal end of said control element extending out of said body through a third aperture, and said control assembly further comprising means for sealing said control element to said body at said third aperture.

* * * * *